(12) United States Patent
Dugalic

(10) Patent No.: US 9,801,810 B1
(45) Date of Patent: Oct. 31, 2017

(54) METHOD OF MAKING A DEPILATORY WAX

(71) Applicant: Natasha Dugalic, Gladwyne, PA (US)

(72) Inventor: Natasha Dugalic, Gladwyne, PA (US)

( * ) Notice: Subject to any disclaimer, the term of this patent is extended or adjusted under 35 U.S.C. 154(b) by 0 days.

(21) Appl. No.: 15/375,459

(22) Filed: Dec. 12, 2016

(51) Int. Cl.
| | | |
|---|---|---|
| *A61Q 9/04* | (2006.01) | |
| *A61K 8/97* | (2017.01) | |
| *A61K 8/92* | (2006.01) | |
| *A61K 8/29* | (2006.01) | |

(52) U.S. Cl.
CPC .................. *A61K 8/97* (2013.01); *A61K 8/29* (2013.01); *A61K 8/922* (2013.01); *A61K 8/927* (2013.01); *A61Q 9/04* (2013.01)

(58) Field of Classification Search
CPC . A61Q 9/04; A61K 8/29; A61K 8/922; A61K 8/927
See application file for complete search history.

(56) References Cited

U.S. PATENT DOCUMENTS

2007/0031360 A1* 2/2007 Gupta ...................... A61K 8/02
424/70.11

* cited by examiner

*Primary Examiner* — Eisa Elhilo
(74) *Attorney, Agent, or Firm* — Michael J. Feigin, Esq.; Feigin & Fridman LLC

(57) ABSTRACT

A depilatory composition for hair removal including beeswax, hydrogenated rosin, gum rosin, titanium dioxide, castor oil, and red or pink color. The composition is used at no lower than 95 degree Fahrenheit and removed at room temperature, easily spread and non-toxic.

18 Claims, No Drawings

METHOD OF MAKING A DEPILATORY WAX

FIELD OF THE DISCLOSED TECHNOLOGY

The disclosed technology relates to a method of making depilatory wax that is removed at room temperature without crumbling and without the use of paper backing.

BACKGROUND OF THE DISCLOSED TECHNOLOGY

Depilatory waxes are compounds that when applied to the skin result in hair removal. Many depilatory waxes require heating to a high temperature, which can pose a safety risk because of the potential for burns. This disclosed depilatory wax only requires heating to between 95 to 102 degrees Fahrenheit to be spread on the skin. Many depilatory waxes are difficult to remove at room temperature; they often crumble, which may result in uneven hair removal. The current technology does not crumble at room temperature. Also many depilatory waxes require an extra strip to pull off both the hair and the product. The current technology does not use an extra strip.

Many depilatory waxes are very sticky and cannot be applied to the skin in a thick layer because the high viscosity does not allow it to be removed from the application tool. Furthermore, depilatory waxes often break many hairs instead of removing them from the root. The currently disclosed depilatory wax does not stick to the application tool while being applied to the skin and therefore can be applied in a thicker layer. Also hairs are removed completely not broken, probably due to the thicker application of the wax to the skin. The lower viscosity during application also results in a wax that is easier to remove from the skin. The current depilatory wax usually comes off in one pull at room temperature and with no paper strip. The ease of pulling the currently disclosed wax off the skin versus traditional wax is remarkable.

Using two types of rosin allows for the wax to be spread easily and uniformly resulting in uniform hair removal. In addition, in the currently disclosed technology there are no toxic ingredients, which can be potentially harmful if absorbed through the skin. The currently disclosed technology often hurts less when pulling off the hair then well known depilatory waxes on the market.

SUMMARY OF THE DISCLOSED TECHNOLOGY

The disclosed technology described herein addresses an unfulfilled need in the prior art by providing a depilatory wax, which removes hair at room temperature, easily spread and is non-toxic.

One Objective of the disclosed technology is a hair removal composition comprising beeswax from about 18 to 20%; hydrogenated rosin from about 35 to 45%; gum rosin from about 35 to 45%. Also titanium dioxide from about 1 to 2%; castor oil from about 2.5 go 3.5%; and color from about 0.05 to 0.20% by weight. The color in the hair removal composition is a red or pink color. 'About' is defined as within 3%. Further, any percentages given in the patent application can be at the actual percentage given, or at 'about' the percentage given, depending on the claim language used.

In another objective of the disclosed technology, the hair removal composition has the beeswax present at about 19 to 20%; the hydrogenated rosin is present at about 37 to 38%; the titanium dioxide is present at about 1 to 2%; castor oil is present at about 3 to 3.5%; and the color is present at about 0.15%.

It is also an objective of the current technology that the method of making the hair removal composition is mixing at room temperature a first mixture of beeswax, hydrogenated rosin, gum rosin. Heating a first mixture until liquefied. Then mixing a second mixture of titanium dioxide, castor oil and color at room temperature. After second mixture is well mixed, it is added to first mixture and all the ingredients are then mixed well; and hair removal composition is then poured into containers where it hardens into hard wax.

In yet another objective, the Method of making a hair removal composition is mixing at room temperature a first mixture of 4.55 Kilograms refined white beeswax, 9 Kilograms hydrogenated rosin, 9 Kilograms gum rosin. First mixture is then heated until liquefied and a second mixture of 360 grams of titanium dioxide, 795 Grams of castor oil and 32 Grams red or pink color is mixed at room temperature. After second mixture is well mixed, it is added to first mixture and all the ingredients are then mixed well. Hair removal composition is then poured into any containers where it hardens into hard wax.

Another objective is method of making a hair removal composition by mixing at room temperature: a first mixture of 19.2% by weight of refined white beeswax, 37.9% by weight of hydrogenated rosin, 37.9% of gum rosin. First mixture is then heated until liquefied. A second mixture of 1.5% by weight of titanium dioxide, 3.35% by weight castor oil and 0.15% by weigh of red or pink color is mixed at room temperature. After second mixture is well mixed, it is added to first mixture and all the ingredients are then mixed well. Then hair removal composition is then poured into any containers where it hardens into hard wax.

In a final objective the first mixtures of all the method of making is heated in a melting machine. The containers filled with the composition are stored in a dry place. The containers used are metal and aluminum. In an alternative the removal composition is then warmed to 95 to 110 degrees Fahrenheit to be placed on skin.

In accordance with these and other objectives, which will become apparent hereinafter, the disclosed technology will now be described with particular reference to the drawings.

DETAILED DESCRIPTION OF EMBODIMENTS OF THE DISCLOSED TECHNOLOGY

The ensuing detailed description provides preferred exemplary embodiments only, and is not intended to limit the scope, applicability, or configuration of the disclosed technology. Rather, the ensuing detailed description of the preferred exemplary embodiments will provide those skilled in the art with an enabling description for implementing the preferred exemplary embodiments of the technology. Various changes may be made in the function and arrangement of elements without departing from the spirit and scope of the disclosed technology, as set forth in the appended claims.

The depilatory wax is a compound of several ingredients which, when mixed in the proportions described below, produces a wax with a viscosity at a temperature as low as 95 degrees Fahrenheit. This allows for easy and even spreading on a skin surface which, when removed, results in hair removal.

The basis of the disclosed depilatory compound comprises two rosin resins. The first is a hydrogenated rosin resin. Hydrogenated rosins are used to enhance the characteristics of the compound. This process is accomplished by adding hydrogen molecules to the double bonds of the rosin acid.

Specifically the hydrogenation process increases the stability of the compound, minimizes skin irritation, minimizes absorption of UV light and lightens the color of the compound. Using the hydrogenated rosin resin makes the depilatory compound gentle on the skin and easy to spread. This rosin has a chemical formula $C_{23}H_{36}O_2$ and preferably is Stabelite Ester 10 trademark name Teckros® H80. This rosin is used in a percentage of 37.9% of the composition by weight.

The second rosin is a gum rosin, known as Brazilian or Chinese gum rosin and has a chemical formula $C_{19}H_{29}COOH$. Its chemical properties are close to those of aliphatic acid, making it fat-soluble. It increases the friction of the compound allowing for improved hair removal. This rosin is used in a percentage of 37.9% of the composition by weight.

Refined white bees wax with a chemical formula of $C_{15}H_{13}COOC_{30}H_{61}$ is also added and comprises 19.2% of the disclosed depilatory compound. The bees wax acts as an emulsifier to prevent separation of the ingredients and also as an emollient adding soothing and softening properties to the depilatory compound making it gentler on the skin.

Castor oil ($C_{54}H_{100}O_7$) is a triglyceride, which is widely used in the skin care industry. Its primary function is as an emollient to help moisturize and soothe the skin. This has the added benefit of providing protection against infection because of its known properties of inhibiting the growth of bacteria, fungi and even viruses according to some sources. These characteristics make this a great addition to the depilatory compound. Castor oil comprises 3.35% by weight of the total depilatory compound.

Titanium dioxide ($TiO_2$) is added as a pigment in a percentage of 1.5% by weight of the total compound. This chemical provides a whitish tint to the compound and is hydrophobic. Additional benefits of using Titanium Dioxide are that it acts as a thickener and provides protection from sun exposure.

Red or pink coloring ($C_{20}H_6O_5I_4NA_3$) is also added for aesthetic purposes in a percentage of 0.15% by weight.

Based on the above, the preferred formulation of the disclosed depilatory wax is as follows: 4.55 Kilograms refined white beeswax, 9 Kilograms hydrogenated rosin, 9 Kilograms Brazilian or Chinese gum rosin, 360 Grams of titanium dioxide, 795 Grams of castor oil and 32 Grams red or pink color. This mixture makes 23.737 Kilograms of the disclosed technology.

The method of making the depilatory wax is preferably done in a melting machine. 4.55 Kilograms of refined white beeswax is mixed with 9 Kilograms of hydrogenated rosin as well as 9 Kilograms Brazilian or Chinese gum rosin. This mixture is heated until it is liquefied. In a different non-heated container 795 Grams of castor oil, 360 Grams of titanium dioxide and 32 Grams of red color are mixed together.

After the castor, titanium dioxide and color are well mixed, they are added to the mixture in the melting machine. All the ingredients are then mixed well and then poured into any containers that are metal and preferably aluminum container where it hardens into hard wax and is stored in a dry place.

The aluminum containers used are preferably 30.48 Centimeters by 22.86 Centimeters and 5.715 Centimeters. Eight aluminum containers are required for 23.737 Kilograms of product. This wax has a very long shelf life. Since the development of the wax, the finished product has not degraded.

Any amounts within the proportions by weight already stated are used in the method of making this unique depilatory compound. Consequently the storage is in any well-known storage containers for depilatory compounds. Preferably the containers are, but not limited to, aluminum containers.

Once made the removal composition is kept at room temperature until needed for hair removal. The removal composition, optionally is then warmed to between 95 to 100 degrees Fahrenheit to be applied to the skin. The removal composition is used alone and does not require any additional strips of paper or cloth to pull off the hair.

It is recognized by those skilled in the art that changes may be made to the above-described embodiments of the disclosed technology without departing from the broad inventive concept thereof. It is understood, therefore, that this technology is not limited to the particular embodiments disclosed but is intended to cover all modifications which are in the spirit and scope of the disclosed technology.

I claim:

1. A hair removal composition comprising:
    A) beeswax from about 18 to 20%;
    B) hydrogenated rosin from about 35 to 45%;
    C) gum rosin from about 35 to 45%;
    D) titanium dioxide from about 1 to 2%;
    E) castor oil from about 2.5 go 3.5%;
    F) and color from about 0.05 to 0.20% by weight.

2. The hair removal composition of claim 1, wherein the color is a red color.

3. The hair removal composition of claim 1, wherein the color is a pink color.

4. The hair removal composition of claim 1, wherein the beeswax is present at about 19 to 20%.

5. The hair removal composition of claim 1, wherein the hydrogenated rosin is present at about 37 to 38%.

6. The hair removal composition of claim 1,
    wherein the method of making is:
        mixing at room temperature a first mixture of beeswax, hydrogenated rosin, and gum rosin;
        heating a first mixture until liquefied;
        mixing a second mixture of titanium dioxide, castor oil and color at room temperature;
        after second mixture is well mixed, it is added to first mixture and all the ingredients are then mixed well; and
        hair removal composition is then poured into containers where it hardens into hard wax.

7. The hair removal composition of claim 1, wherein castor oil is present at about 3 to 3.5%.

8. The hair removal composition of claim 1, wherein color is present at about 0.15%.

9. The hair removal composition of claim 6, wherein the titanium dioxide is present at about 1 to 2%.

10. Method of making a hair removal composition by mixing at room temperature:
    a first mixture of 4.55 Kilograms refined white beeswax, 9 Kilograms hydrogenated rosin, and 9 Kilograms gum rosin;
    first mixture is then heated until liquefied; and
    a second mixture of 360 grams of titanium dioxide, 795 Grams of castor oil and 32 Grams red or pink color is mixed at room temperature;
    after second mixture is well mixed, it is added to first mixture and all the ingredients are then mixed well; and hair removal composition is then poured into containers where it hardens into hard wax.

11. Method of making a hair removal composition by mixing at room temperature:
   a first mixture of 19.2% by weight of refined white beeswax, 37.9% by weight of hydrogenated rosin, and 37.9% of gum rosin;
   first mixture is then heated until liquefied; and
   a second mixture of 1.5% by weight of titanium dioxide, 3.35% by weight castor oil and 0.15% by weigh of red or pink color is mixed at room temperature;
   after second mixture is well mixed, it is added to first mixture and all the ingredients are then mixed well; and
   hair removal composition is then poured into containers where it hardens into hard wax.

12. Method of making a hair removal composition by mixing at room temperature:
   a first mixture of 4.55 Kilograms refined white beeswax, 9 Kilograms hydrogenated rosin, and 9 Kilograms gum rosin;
   first mixture is then heated until liquefied; and
   a second mixture of 360 grams of titanium dioxide, 795 Grams of castor oil and 32 Grams red or pink color is mixed at room temperature;
   after second mixture is well mixed, it is added to first mixture and all the ingredients are then mixed well;
   hair removal composition is then poured into containers where it hardens into hard wax; and
   the removal composition is warmed to between 95 to 100 degrees Fahrenheit to be applied to the skin.

13. The method of claim 12, wherein the first mixture is heated in a melting machine.

14. The method of claim 10, wherein the first mixture is heated in a melting machine.

15. The method of claim 12, wherein the containers filled with the composition is stored in a dry place.

16. The method of claim 10, wherein the containers filled with the composition is stored in a dry place.

17. The method of claim 6, wherein the first mixture is heated in a melting machine.

18. The method of claim 6, wherein the containers filled with the composition are aluminum metal and are stored in a dry place.

* * * * *